(12) United States Patent
Philbin

(10) Patent No.: US 11,045,412 B2
(45) Date of Patent: Jun. 29, 2021

(54) SKIN CARE FORMULATIONS

(71) Applicant: Akzo Nobel Chemicals International B.V., Amersfoort (NL)

(72) Inventor: Michael Timothy Philbin, Hopewell, NJ (US)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 14/650,423

(22) PCT Filed: Dec. 19, 2013

(86) PCT No.: PCT/EP2013/077288
§ 371 (c)(1),
(2) Date: Jun. 8, 2015

(87) PCT Pub. No.: WO2014/096131
PCT Pub. Date: Jun. 26, 2014

(65) Prior Publication Data
US 2015/0328129 A1    Nov. 19, 2015

Related U.S. Application Data

(60) Provisional application No. 61/740,602, filed on Dec. 21, 2012.

(30) Foreign Application Priority Data

Mar. 22, 2013    (EP) ..................................... 13160545

(51) Int. Cl.
    *A61K 8/81*      (2006.01)
    *A61Q 17/04*      (2006.01)
    *C09D 133/26*      (2006.01)

(52) U.S. Cl.
CPC ............ *A61K 8/8158* (2013.01); *A61Q 17/04* (2013.01); *C09D 133/26* (2013.01); *A61K 2800/54* (2013.01); *A61K 2800/591* (2013.01)

(58) Field of Classification Search
CPC .................. A61Q 17/04; A61K 8/8158; A61K 2800/591; A61K 2800/54; C09D 133/26
See application file for complete search history.

(56) References Cited

U.S. PATENT DOCUMENTS

| 3,927,199 | A | 12/1975 | Micchelli et al. | |
|---|---|---|---|---|
| 3,930,865 | A | 1/1976 | Faust et al. | |
| 4,293,635 | A | 10/1981 | Flint et al. | |
| 4,423,199 | A | 12/1983 | Chang et al. | |
| 4,842,852 | A | 6/1989 | Nowak, Jr. et al. | |
| 5,288,493 | A * | 2/1994 | Martino ............... | A61K 8/8158 424/401 |
| 5,576,403 | A | 11/1996 | Chandran et al. | |
| 5,599,524 | A | 2/1997 | Morawsky et al. | |
| 6,139,827 | A | 10/2000 | Cohen et al. | |
| 6,159,481 | A | 12/2000 | Fallick | |
| 6,231,837 | B1 | 5/2001 | Stroud et al. | |
| 6,261,541 | B1 | 7/2001 | Karpov et al. | |
| 6,482,393 | B1 | 11/2002 | Schehlmann et al. | |
| 6,482,397 | B1 | 11/2002 | Scott et al. | |
| 6,488,916 | B1 | 12/2002 | Fowler | |
| 7,008,618 | B1 * | 3/2006 | Hessefort ............. | A61K 8/8158 424/400 |
| 2002/0076390 | A1 | 6/2002 | Kantner et al. | |
| 2004/0042994 | A1 * | 3/2004 | Dausch ................ | A61K 8/8188 424/70.16 |
| 2004/0258644 | A1 | 12/2004 | Simonnet | |
| 2006/0104923 | A1 | 5/2006 | Shah et al. | |
| 2006/0252877 | A1 | 11/2006 | Farwaha et al. | |
| 2010/0272657 | A1 | 10/2010 | He et al. | |
| 2012/0195839 | A1 | 8/2012 | He et al. | |

FOREIGN PATENT DOCUMENTS

| GB | 1 557 580 A | 12/1979 |
|---|---|---|
| WO | 94/02112 A1 | 2/1994 |

OTHER PUBLICATIONS

European Search Report dated Sep. 4, 2013, issued in European Application No. 13 16 0545.3.
Notification of Transmittal of the International Search Report and Written Opinion issued from the International Bureau of WIPO for International Application No. PCT/EP2013/077288, dated Apr. 2, 2014.

\* cited by examiner

*Primary Examiner* — Doan T Phan
(74) *Attorney, Agent, or Firm* — Norris McLaughlin, P.A.

(57) ABSTRACT

A skin care formulation includes at least one polymer and at least one sunscreen active agent and provides low tack and an improved sun protection factor. The polymer is derived from at least one acid-containing monomer, at least one N-alkyl(meth)acrylamide monomer, and, optionally, at least one alkyl(meth)acrylate monomer.

6 Claims, No Drawings

SKIN CARE FORMULATIONS

This application is a national stage filing under 35 U.S.C. §371 of PCT/EP2013/077288, filed Dec. 19, 2013, which claims priority to U.S. Provisional Patent Application No. 61/740,602 filed Dec. 21, 2012, and European Patent Application No. 13160545.3, filed Mar. 22, 2013, the contents of which are each incorporated herein by reference in their entireties.

FIELD OF THE INVENTION

The present invention relates to skin care formulations comprising at least one polymer derived from at least one acid-containing monomer and at least one N-alkyl(meth)acrylamide monomer, and at least one sunscreen active agent that provide low tack and increased sun protection factor (SPF).

BACKGROUND OF THE INVENTION

Skin care formulations, such as sunscreens, are typically categorized as either aqueous or non-aqueous, i.e., anhydrous, compositions. Aqueous sunscreen compositions are typically provided as creams formed as emulsions containing active UV absorbing compounds and additional ingredients, such as waterproofing agents, fragrances, emollients and other skin care ingredients. Non-aqueous sunscreen compositions are typically provided as solvent-based compositions that can be formed as gels for topical application or sprayed-on, for example from an alcohol based solution of the ingredients.

Sprayable sunscreen compositions have become popular in recent years as a means for transporting and applying sunscreen. Film forming polymers are known to be added to non-aqueous sunscreen compositions so as to provide water resistance to these sunscreen compositions after the compositions are applied to the skin or hair. However, conventional film forming polymers used in spray-on sunscreens suffer from a tacky feel when the sunscreen formulation has dried.

Accordingly, there is a need to provide film forming polymers for use in skin care formulations that provide a lower tack with equivalent or improved sun protection. Lower tack translates to better feel on the skin of the user.

SUMMARY OF THE INVENTION

In an aspect, the invention relates to a skin care formulation comprising at least one polymer and at least one sunscreen active agent. The at least one polymer is derived from at least one acid-containing monomer and at least one alkyl acrylamide monomer. The acid-containing monomer may be present from about 5 to about 35 weight percent of the total monomer content in the polymer and the N-alkyl (meth)acrylamide monomer may be present from about 27 to about 88 percent of the total weight of the monomer content in the polymer.

DETAILED DESCRIPTION OF THE INVENTION

The present invention generally relates to skin care formulations that include at least one film forming polymer that provides low tack and an increased sun protection factor. In an aspect, the present invention therefore relates to a skin care formulation comprising a polymer derived from at least one acid-containing monomer and at least one N-alkyl (meth)acrylamide monomer. The skin care formulation optionally comprises at least one alkyl(meth)acrylate.

In an embodiment of the invention, the film forming polymers contain at least one acid-containing monomer. Some non-limiting examples of these acid-containing monomers include maleic acid, fumaric acid, acrylic acid, methacrylic acid, itaconic acid. Also suitable are $C_1$-$C_4$ alkyl half esters of maleic and fumaric acids such as methyl hydrogen maleate and butyl hydrogen fumarate, as well as any other acidic monomers which are capable of being copolymerized with the particularly desired polymeric binder system. As is known to those of ordinary skill in the art, the acidic co-monomer(s) must be chosen so that they are readily polymerizable with the polymer. In an embodiment, the acid-containing monomer(s) are acrylic acid, methacrylic acid, crotonic acid, itaconic acid and maleic acid. Mixtures of the various above-described monomers may also be used. In a preferred embodiment, the acid-containing monomer is methacrylic acid.

In an embodiment, the amount of acid-containing monomer present in the polymers of this invention is in the range from about 5 to about 35 weight percent based on total monomer content in the dry polymer. In another embodiment, the acid-containing monomer is present from about 10 to about 25 weight percent based on total monomer content in the dry polymer, and in another embodiment about 12 to about 23 percent. In still another embodiment, the acid-containing monomer is present in the polymer from about 12 to about 16 percent based on total monomer content in the dry polymer. In yet another embodiment, the acid-containing monomer is present from greater than 16 to about 23 percent of the total monomer content in the dry polymer.

In an embodiment of the invention, the film forming polymers contain at least one N-alkyl(meth)acrylamide monomer. These monomers may contain from about 2 to about 12 carbon atoms in the alkyl group. Some non-limiting examples of suitable acrylamides include N-t-octyl acrylamide, N-butyl acrylamide, N-methyl acrylamide, methacrylamide, N-n-butyl acrylamide, N-n-octyl acrylamide, N-t-butyl acrylamide and N-t-octylacrylamide, as well as mixtures thereof. In an embodiment, the acrylamides may be N-substituted acrylamides or N-substituted methacrylamides substituted with alkyl radicals containing from 2-12 carbon atoms. In a further embodiment, the applicable acrylamides and methacrylamides include N-ethyl acrylamide, N-decyl acrylamide, N-dodecyl acrylamide and mixture thereof, as well as the corresponding methacrylamides and mixtures thereof. Optionally, mixtures of the above-described acrylamides or methacrylamides may also be used. In an embodiment, the N-substituted acrylamide or N-substituted methacrylamide is N-tert.-octyl acrylamide. In an embodiment of the current invention the co-polymer may contain a mixture of one or more hydrophobic monomers. In a preferred embodiment, the N-alkyl(meth)acrylamide monomer is N-n-octyl acrylamide or N-t-octyl acrylamide.

In an embodiment, the amount of N-alkyl(meth)acrylamides present in the polymers of the current invention may be from about 27 percent to about 88 percent by weight based on total weight of the dry polymer. In another embodiment, the N-alkyl(meth)acrylamides are present from about 35 percent to about 85 percent of the total dry weight of the polymer. In another embodiment, the N-alkyl(meth)acrylamide may be present from about 60 to about 85 percent of the total monomer content in the dry polymer.

In another embodiment, it may be desirable to have an optional alkyl(meth)acrylate monomer included into the polymers of this invention. The alkyl group of the alkyl (meth)acrylate may contain from about 1 to about 8 carbon atoms and are uncharged (i.e. nonionic). Some non-limiting examples of suitable alkyl(meth)acrylates include methyl acrylate, butyl acrylate, ethyl acrylate, methyl methacrylate, ethyl methacrylate, n-butyl methacrylate, iso-butyl methacrylate and n-octyl methacrylate as well as mixtures thereof. In an embodiment, the alkyl acrylate may be n-butyl acrylate, iso-butyl acrylate, n-butyl methacrylate, iso-butyl methacrylate or n-octyl methacrylate.

In an embodiment, the alkyl(meth)acrylate monomers may be present in the amount up to about 55 percent by weight of the total monomer content in the dry polymer. In another embodiment, the alkyl(meth)acrylate will be present from about 0 to about 20 percent by weight of the monomer content in dry polymer. In yet another embodiment the alkyl(meth)acrylate is present from about 1 to about 55 percent by weight of the total monomer content in the polymer. In still yet another embodiment, the alkyl(meth) acrylate is present from about 1 to about 20 percent of the total monomer content in the dry polymer. In another embodiment, the alkyl(meth)acrylate monomers are present in an amount from about 5 to about 30 percent by weight based on total weight of the monomer content in the dry polymer. In still yet another embodiment, the alkyl(meth) acrylate is present from about 30 to about 55 percent of the total monomer content in the dry polymer.

Skin care formulations that include the polymers of the present invention provide improved (less) tack when applied to the skin and increased sun protection factor (SPF) to the skin as compared to conventional polymers currently on the market. One such polymer, used as the industry standard, is Acrylates/Octylacrylamide Copolymer (sold as Dermacryl® 79 by Akzo Nobel Surface Chemistry LLC, Bridgewater, N.J.).

The film forming polymers according to the present invention can be characterized by their ability to give low tack films on the skin. Tack, for purposes of this invention is measured using a TA XT Plus Texture Analyzer (Texture Technologies Scarsdale, N.Y.) as described in the experimental section, below. In an embodiment, the film forming polymers of the present invention will provide a tack of less than about 450 gmf compared to skin care formulations that include the control (i.e., acrylates/octylacrylamide copolymer), which give about 460 gmf. In another embodiment of the invention, the tack will be about 400 gmf or less, and in still another embodiment, the tack will be about 375 gmf or less. Alternatively, in an embodiment of the invention, the tack of a skincare formulation (including sunscreen active agents) comprising the film forming polymers of the present invention will be lower than the tack of the same skin care formulation that comprises an acrylates/octylacrylamide copolymer, where the only difference between the respective skincare formulations is the film forming polymer. In another embodiment, the tack will be about 1% or more lower than the tack of the same skin care formulation that comprises an acrylates/octylacrylamide copolymer, in still another embodiment, about 50% or more, lower.

In an embodiment of the invention, the polymer is present in an amount of about 0.1% to about 8% by weight of the formulation. In another embodiment, the polymer is present in an amount of 0.5% to about 5% by weight of the formulation, and in another embodiment in an amount of 1% to about 3% by weight of the formulation.

Additional film forming polymers, either synthetic or natural can also optionally be used in combination with the inventive polymers described above. Non-limiting examples of these additional film forming polymers are: from National Starch and Chemical Company, AMPHOMER® and AMPHOMER® LV-71 polymers (octylacrylamide/acrylates/butylaminoethyl methacrylate copolymer), AMPHOMER® HC polymer (acrylates/octylacrylamide copolymer) BALANCE® 0/55 and BALANCE® CR polymers (acrylates copolymer), BALANCE® 47 polymer (octylacrylamide/butylaminoethyl methacrylate copolymer), RESYN® 28-2930 polymer (VA/crotonates/vinyl neodecanoate copolymer), RESYN® 28-1310 polymer (VA/Crotonates copolymer), FLEXAN® polymers (sodium polystyrene sulfonate), DynamX polymer (polyurethane-14 (and) AMP-Acrylates copolymer), RESYN® XP polymer (acrylates/octylacrylamide copolymer), STRUCTURE® 2001 (acrylates/steareth-20 itaconate copolymer) and STRUCTURE® 3001 (acrylates/ceteth-20 itaconate copolymer); from ISP, OMNIREZ-2000® (PVM/MA half ethyl ester copolymer), GANEX P-904® (butylated PVP), GANEX V-216® (PVP/hexadecene copolymer) GANEX® V-220 (PVP/eicosene copolymer), GANEX® WP-660 (tricontanyl PVP), GANTREZ® A425 (butyl ester of PVM/MA copolymer), GANTREZ® AN-119 PVM/MA copolymer, GANTREZ® ES 225 (ethyl ester of PVM/MA copolymer), GANTREZ® ES425 (butyl ester of PVM/MA copolymer), GAFFIX® VC-713 (vinyl caprolactam/PVP/dimethylaminoethyl methacrylate copolymer), GAFQUAT® 755 (polyquatemium-11), GAFQUAT HS-100® (polyquatemium-28) AQUAFLEX® XL-30 (Polyimide-1), AQUAFLEX® SF-40 (PVP/Vinylcaprolactam/DMAPA Acrylates Copolymer), AQUAFLEX® FX-64 (Isobutylene/Ethylmaleimide/Hydroxyethylmaleimide Copolymer), ALLIANZ® LT-120 (Acrylates/C1-2 Succinates/Hydroxyacrylates Copolymer), STYLEZE® CC-10 (PVP/DMAPA Acrylates Copolymer), STYLEZE® 2000 (VP/Acrylates/Lauryl Methacrylate Copolymer), STYLEZE® W-20 (Polyquaternium-55), Copolymer Series (PVP/Dimethylaminoethylmethacrylate Copolymer), ADVANTAGE® S and ADVANTAGE® LCA (VinylcaprolactamNP/Dimethylaminoethyl Methacrylate Copolymer), ADVANTAGE® PLUS (VA/Butyl Maleate/Isobornyl Acrylate Copolymer); from BASF, ULTRAHOLD STRONG (acrylic acid/ethyl acrylate/t-butyl acrylamide), LUVIMER® 100P (t-butyl acrylate/ethyl acrylate/methacrylic acid), LUVIMER® 36D (ethyl acrylate/t-butyl acrylate/methacrylic acid), LUVIQUAT® HM-552 (polyquaternium-16), LUVIQUAT® HOLD (polyquatemium-16), LUVISKOL® K30 (PVP) LUVISKOL® K90 (PVP), LUVISKOL® VA 64 (PVP/VA copolymer) LUVISKOL® VA73W (PVP/VA copolymer), LUVISKOL® VA, LUVISET® PUR (Polyurethane-1), LUVISET® Clear (VP/MethacrylamideNinyl Imidazole Copolymer), LUVIFLEX® SOFT (Acrylates Copolymer), ULTRAHOLD® 8 (Acrylates/Acrylamide Copolymer), LUVISKOL® Plus (Polyvinylcaprolactam), LUVIFLEX® Silk (PEG/PPG-25/25 Dimethicone/Acrylates Copolymer); from Amerchol, AMERHOLD® DR-25 (acrylic acid/methacrylic acid/acrylates/methacrylates); from Rohm&Haas, ACUDYNE® 258 (acrylic acid/methacrylic acid/acrylates/methacrylates/hydroxy ester acrylates; from Mitsubishi and distributed by Clariant, DIAFORMER® Z-301, DIAFORMER® Z-SM, and DIAFORMER® Z-400 (methacryloyl ethyl betaine/acrylates copolymer), ACUDYNE® 180 (Acrylates/Hydroxyesters Acrylates Copolymer), ACUDYNE® SCP (Ethylenecarboxyamide/AMPSA/Methacrylates Copolymer), and the ACCLTLYN® rheological modifiers; from ONDEO Nalco, FIXOMER® A-30 and FIXOMER® N-28 (INCI names: methacrylic acid/sodium acrylamidomethyl propane sulfonate copolymer); from Noveon, FIXATE® G-100 (AMP-Acrylates/Allyl Methacrylate Copolymer), FIXATE PLUS® (Polyacrylates-X), CARBOPOL® Ultrez 10 (Carbomer), CARBOPOL® Ultrez 20 (Acrylates/C10-30 Alkyl Acrylates Copolymer), AVALURE® AC series (Acrylates Copolymer), AVALURE® UR series (Polyurethane-2, Polyurethane-4, PPG-17/IPDI/DMPA Copolymer); polyethylene glycol; water-soluble acrylics; water-soluble polyesters; polyacrylamides; polyamines; polyquatemary amines; styrene maleic anhydride (SMA) resin; polyethylene amine; and other conventional polymers that are polar solvent soluble or that can be made soluble through neutralization with the appropriate base.

Additional natural film forming polymers include native starch as used herein, also starches derived from a plant obtained by standard breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein.

One skilled in the art would recognize that the film forming polymers may further comprise a blend of two of more polymers. In one example embodiment of the invention, a blend of polymers may be used, wherein at least one of the polymers contains a carboxylic acid monomer and the level of carboxylic acid monomer is no less than 5% of the total polymer (by weight dry basis of the total film forming polymer).

Sunscreen compositions according to the invention are prepared as aqueous volatile solvent-based compositions, meaning non-emulsion compositions containing primarily volatile solvents and up to about 30% by weight water. Thus, the compositions comprise a single liquid phase that may further comprise dispersed particulates. In certain embodiments, the compositions of the invention contain up to about 25% by weight water or up to about 20% by weight water, or about 1% to about 25% by weight water or about 1% to about 20% by weight water. In additional embodiments of the invention the compositions comprise between about 10% and about 30% by weight water, between about 10% and about 25% water or between about 10% and about 20% water. Example volatile solvents include one or more of alcohols such as methanol, ethanol and isopropanol, volatile hydrocarbons such as isooctane, isododecane, and isohexadecane, aldehydes and volatile silicones also including volatile ketones such as acetone and methyl ethyl ketone. In an embodiment of this invention the volatile solvent is chosen from the group consisting of ethanol, methanol, isopropanol and acetone. The sunscreen compositions of the invention containing alcohol based solvent systems are characterized as non-aqueous solutions. However, it may be desirable to have a small amount of water in the composition, for example as a processing aid or co-solvent. In certain example embodiments, the water contents of the compositions will be no greater than about 9% water so as to prevent the active to phase separate or precipitate out of solution. Those of ordinary skill in the art will recognize that different actives have different tolerance for water in solution and will adjust water content accordingly. Additionally, the solvent can include an oil such as mineral or vegetable oil. The oil may be the only solvent or may be used in varying amounts as a co-solvent or as described herein as "emollients".

For purposes of the present invention, a "sunscreen active agent" or "sunscreen active" shall include all of those materials, singly or in combination, that are regarded as acceptable for use as active sunscreen ingredients based on their ability to absorb UV radiation. Such compounds are generally described as being UV-A, UV-B, or UV-A/UV-B active agents. Approval by a regulatory agency is generally required for inclusion of active agents in formulations intended for human use. Those active agents which have been or are currently approved for sunscreen use in the United States include organic and inorganic substances including, without limitation, para aminobenzoic acid, avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum. Examples of additional sunscreen actives that have not yet been approved in the US but are allowed in formulations sold outside of the US include ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. However, as the list of approved sunscreens is currently expanding, those of ordinary skill in the art will recognize that the invention is not limited to sunscreen active agents currently approved for human use but is readily applicable to those that may be allowed in the future.

In an embodiment of the invention, the sunscreen active agents are present in an amount of about 50% or less by weight of the formulation. In another embodiment, the sunscreen active agents are present in an amount of about 40% or less, and in still another embodiment, in an amount of about 30% or less by weight of the formulation, and in still yet another embodiment, in an amount of about 25% or less by weight of the formulation.

The polymers of this invention can also provide improved SPF protection when added to a wide variety of UV absorbing materials as listed above. The SPF of the formulations with polymers of this invention will be at least 10% greater than compared to the same formulation that includes the acrylates/octylacrylamide copolymer as the polymer. In an embodiment of this invention, the SPF of the formulation containing the polymers of the present invention will be at least 15% greater, particularly 20% greater than the same formulation containing acrylates/octylacrylamide copolymer.

In one embodiment of the invention the sunscreen active agent comprises a photoprotecting effective amount of particulates of at least one inorganic pigment or nanopigment, non-limiting examples of which include titanium dioxide, zinc oxide, iron oxide, zirconium oxide, cerium oxide, or mixture thereof.

The compositions of this invention can be applied to the skin as a liquid rub on, but are most commonly applied as a spray. However, the compositions are not limited to those compositions applied to the skin primarily as a sunscreen agent. The compositions also incorporate those formulations where the sunscreen active agent is an ingredient in another topically applied composition. Some non-limiting examples are lipstick, make-up, lip-balm, eye-shadow, hair dyes and conditioners, or any application where sun protection may be deemed beneficial.

In certain embodiments of the subject invention, the compositions can be stored in containers under pressure by combination with a propellant. The compositions thus stored can be applied by opening a valve in the container releasing the propellant and the composition, typically in a spray or mist. The propellant used in the composition may be any suitable gas, or combination of gasses, that can be compressed or liquefied within a dispensing spray canister, which expand or volatilize to vapor or gas form upon exposure to ambient temperature and pressure conditions to deliver the composition in an aerosol form. Suitable propellants include hydrocarbons having 1 to 5 carbon atoms, including but not limited to methane, ethane, propane, isopropane, butane, isobutane, butene, pentane, isopentane, neopentane, pentene, hydrofluorocarbons (HFCs), chlorofluorocarbons (CFCs), nitrogen, ethers including dimethyl ether, and any mixtures thereof. Those of ordinary skill in the art recognize that in a closed container such as an aluminum can or glass bottle, propellants such as dimethyl ether condense to the liquid state at ambient temperature. Thus, the composition in the aerosol container is liquid formulation which can contain dissolved propellant, undissolved liquid propellant and gaseous propellant. All of this is under pressure due to the vapor pressure of the propellant. In the practice of this aspect of the subject invention, the propellant can be present in an amount up to about 90 weight percent, preferably from about 2 weight percent to about 50 weight percent, and more preferably about 5 weight percent to about 40 weight percent, more preferably at about 30 weight percent, based on the total weight of the aerosol composition.

The compositions of the present invention may contain a wide range of additional, optional components which are referred to herein as "cosmetic components", but which can also include components generally known as pharmaceutically active agents. The CTFA Cosmetic Ingredient Handbook, Seventh Edition, 1997 and the Eighth Edition, 2000, which is incorporated by reference herein in its entirety, describes a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, SPF boosters, waterproofing agents, and viscosity increasing agents (aqueous and nonaqueous).

The compositions of the invention may also include materials that also increase the SPF of the final composition by such mechanisms as UV radiation scattering and dispersion. Such materials are referred to herein as "UV-radiation scattering agents" and comprise materials that exhibit UV absorbing activity or exhibit no UV absorbing activity. An example of such UV-radiation scattering agents include polymeric materials, such as the product known as Sun-Spheres™ (Rohm and Haas; Philadelphia, Pa.) which are described by their manufacturer as hollow styrene/acrylates copolymer spheres manufactured by emulsion polymerization. The polymer spheres are said to raise SPF values across the UVA and UVB region by dispersing and/or scattering the incident UV radiation throughout the film of sunscreen present on a surface, such as human skin. It is understood that the spheres cause less UV radiation to penetrate into the skin by redirecting the radiation towards the UV-absorbing sunscreen actives in the sunscreen formulation, where the radiation reacts with the sunscreen active molecules and the energy is dissipated as heat. As used herein, the terms "spheres" or "scattering agents" are not limited by chemical makeup or shape, but comprise any agent that produces the effect of lengthening the path of incident UV radiation, increasing the statistical likelihood that the radiation will contact a sunscreen active molecule, i.e., a UV absorbing active agent. These materials may also include UV absorbing materials that also exhibit scattering properties such as ZnO (examples include Z-Cote™ products available from BASF), $TiO_2$ (examples include the Solaveil™ products available from Uniqema (New Castle, Del., USA)), compounds such as methylene bis-benzotriazolyl tetramethylbutylphenol, ("Tinasorb™ M" available from Ciba Specialty Chemicals, Inc. (Basel, Switzerland). UV radiation scattering agents are typically present in the formulation in amounts up to about 25% by weight. Certain example embodiments of the invention may comprise up to about 10% by weight, preferably in ranges of about 0.5% to about 7.0% by weight, in particularly preferred ranges of 3% to about 5% by weight.

As used herein, the terms "sunless-tanning agent" or "self-tanning compositions" refer to compositions which, when applied to human skin, impart thereto an appearance similar to that achieved by exposing the skin to natural or artificial sunlight. Examples of sunless tanning active agents are described in U.S. Pat. Nos. 6,482,397, 6,261,541, and 6,231,837. Such sunless tanning compositions typically comprise, in addition to an artificial tanning effective amount of a self tanning agent, effective amounts of a composition coloring agent and a cosmetically acceptable carrier adapted for topical application to human skin. The self tanning agents can also include those compositions generally accepted in the art for application to human skin, and which, when so applied, react therein with amino acids so as to form pigmented products. Such reactions give the skin a brown appearance similar to the color obtained upon exposing it to sunlight for periods of time sufficient to tan the skin. Suitable self tanning agents include, without limitation, alpha-hydroxy aldehydes and ketones, glyceraldehyde and related alcohol aldehydes, various indoles, imidazoles and derivatives thereof, and various approved pigmentation agents. Presently preferred herein as self tanning agents are the alpha-hydroxy aldehydes and ketones. Most preferably, the self tanning agent is dihydroxyacetone ("DHA"). Other suitable self tanning agents include, without limitation, methyl glyoxal, glycerol aldehyde, erythrulose, alloxan, 2,3-dihydroxysuccindialdehyde, 2,3-dimethoxysuccindialdehyde, 2-amino-3-hydroxy-succindialdehyde and 2-benzylamino-3-hydroxysuccindialdehyde.

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil, grape seed oil, sweet almond oil, and peanut oil. Preferably, the emollient is a cocoglyceride, which is a mixture of mono, di- and triglycerides of cocoa oil, sold under the trade name of Myritol 331 from Henkel KGaA, or Dicaprylyl Ether available under the trade name Cetiol OE from Henkel KGaA or a $C_{12}$-$C_{15}$ Alkyl Benzoate sold under the trade name Finsolv TN from Finetex. One or more emollients may be present ranging in amounts from about 1 percent to about 10 percent by weight, preferably about 5 percent by weight. Another suitable emollient is DC 200 Fluid 350, a silicone fluid, available Dow Corning Corp.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the formulation.

A humectant is a moistening agent that promotes retention of water due to its hygroscopic properties. Suitable humectants include glycerin, polymeric glycols such as polyethylene glycol and polypropylene glycol, mannitol and sorbitol. Preferably, the humectant is Sorbitol, 70% USP or polyethylene glycol 400, NF. One or more humectants can optionally be included in the formulation in amounts from about 1 percent to about 10 percent by weight, preferably about 5 percent by weight.

A dry-feel modifier is an agent which when added to an emulsion, imparts a "dry feel" to the skin when the emulsion dries. Dry feel modifiers can include talc, kaolin, chalk, zinc oxide, silicone fluids, inorganic salts such as barium sulfate, surface treated silica, precipitated silica, fumed silica such as an Aerosil available from Degussa Inc. of New York, N.Y. U.S.A. Another dry feel modifier is an epichlorohydrin cross-linked glyceryl starch of the type that is disclosed in U.S. Pat. No. 6,488,916.

It may be advantageous to incorporate additional thickening agents, such as, for instance, various Carbopols available from Noveon Co. Particularly preferred are those agents which would not disrupt the lamellar structure in the formulation of the final product, such as non-ionic thickening agents. The selection of additional thickening agents is well within the skill of one in the art.

Additional natural or synthetic substances can also be added to the compositions of the invention to protect from or delay its deterioration due to the action of oxygen in the air (oxidation). They may also reduce oxidation reactions in skin tissue. Such substances prevent oxidative deterioration which may lead to the generation of rancidity and nonenyzymatic browning reaction products. Typical suitable substances include propyl, octyl and dodecyl esters of gallic acid, butylated hydroxyanisole (BHA, usually purchased as a mixture of ortho and meta isomers), butylated hydroxytoluene (BHT), green tea extract, uric acid, cysteine, pyruvate, nordihydroguaiaretic acid, Vitamin A, Vitamin E and Vitamin C and their derivatives. One or more such substances can optionally be included in the composition in an amount ranging from about 0.001 to about 5 weight percent, preferably about 0.01 to about 0.5 percent.

Chelating agents are substances used to chelate or bind metallic ions, such as with a heterocylic ring structure so that the ion is held by chemical bonds from each of the participating rings. Suitable chelating agents include ethylene diaminetetraacetic acid (EDTA), EDTA disodium, calcium disodium edetate, EDTA trisodium, albumin, transferrin, desferoxamine, desferal, desferoxamine mesylate, EDTA tetrasodium and EDTA dipotassium, or combinations of any of these.

Fragrances are aromatic substances which can impart an aesthetically pleasing aroma to the sunscreen composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. One or more fragrances can optionally be included in the sunscreen composition in an amount ranging from about 0.001 to about 5 weight percent, preferably about 0.01 to about 0.5 percent by weight.

Additional preservatives may also be used if desired and include well known preservative compositions such as benzyl alcohol, phenyl ethyl alcohol and benzoic acid, diazolydinyl, urea, chlorphenesin, iodopropynyl and butyl carbamate, among others.

The compositions of the invention can further comprise skin protectant active agents. Suitable examples include (with preferred weight percent ranges), Allantoin (0.5 to 2 percent); Aluminum hydroxide gel (0.15 to 5 percent); Calamine (1 to 25 percent); Cocoa butter (greater than 50); Cod liver oil (5 to 14 percent); Colloidal oatmeal; Dimethicone (1 to 30 percent); Glycerin (20 to 45 percent); Hard fat (greater than 50); Kaolin (4 to 20 percent); Lanolin (12.5 to 50 percent); Mineral oil (greater than 50 percent); Petrolatum (greater than 30 percent); Sodium bicarbonate; Topical starch (10 to 98 percent); White petrolatum (greater than 30 percent); Zinc acetate (0.1 to 2 percent); Zinc carbonate (0.2 to 2 percent); and Zinc oxide (1 to 25 percent).

The compositions of the invention may further include insect repelling components. The most widely used insect repelling active agent for personal care products is N,N-Diethyl-m-toluamide, frequently called "DEET" and available in the form of a concentrate containing at least about 95 percent DEET. Other synthetic chemical repellents include ethyl butylacetylaminoproprionate (also known as IR 3535), dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

Topical application of the compositions of the invention described herein to the hair or skin of a human will provide enhanced protection against deleterious effects of ultraviolet radiation (UVR). Thus, the subject invention further provides a method for protecting human skin and/or hair against the deleterious effects of solar radiation, more particularly UVR, which method comprises topically applying thereto an effective amount of the compositions as described herein. An esthetically beneficial result of exposure of skin to UVR (i.e., light radiation wavelengths of from 280 nm to 400 nm) is the promotion of tanning of the human epidermis. Another benefit of sun exposure comes from production of vitamin D within the skin. UVR is typically divided into UV-A (light wavelengths from 320 to 400 nm) and UV-B (wavelengths ranging from 280 to 320 nm) regions. Overexposure to UV-B irradiation is generally understood to lead to skin burns and erythema. In addition, overexposure to UV-A radiation may cause a loss of elasticity of the skin and the appearance of wrinkles, promoting premature skin aging. Such irradiation promotes triggering of the erythemal reaction or amplifies this reaction in certain individuals and may even be the source of phototoxic or photoallergic reactions. It is increasingly believed that overexposure to UV-A may also lead to melanoma. Thus, the application of the compositions of the invention to the skin and/or hair of an individual will provide enhanced UVR photoprotection (UV-A and/or UV-B) of the skin and/or hair of the individual.

The sunscreen containing compositions of the invention are intended to provide a sun protection factor (SPF) rating of at least 2, with additional preferable embodiments having a sun protection factor of at least 5, in another embodiment at least 10, in another embodiment at least 15, in another embodiment at least 20, in another embodiment at least 25, in another embodiment at least 30, in another embodiment at least 35, in another embodiment at least 40, in another embodiment at least 45, in another embodiment at least 50, in another embodiment at least 55, in another embodiment at least 60, in another embodiment at least 65, in another embodiment at least 70, in another embodiment at least 75, in another embodiment at least 80, in another embodiment at least 85, in another embodiment at least 90, in another embodiment at least 95, and in another embodiment at least 100.

The present invention is useful for increasing the SPF and lowering tack in skin care formulations, such as sunscreens. It also further provides a method of reducing the deleterious effects of UV radiation that contacts a surface which comprises applying to the surface the compositions of the invention. In addition, the invention also provides a method of preventing or reducing the occurrence of erythema on a subject due to exposure to UV radiation, or a method of preventing or reducing the occurrence of phototoxic or photoallergic reactions in a subject due to exposure to UV radiation, each of which comprises applying the composition of the invention to the subject prior to exposure to UV radiation.

In another aspect, the invention provides a method for preparing skin care formulations comprising mixing at least one polymer and at least one sunscreen active agent, wherein the polymer is derived from at least one acid-containing monomer and at least one N-alkyl(meth)acrylamide monomer. Further, the acid-containing monomer is present in the polymer from about 12 to about 23 weight percent of the total monomer content in the polymer and the N-alkyl(meth) acrylamide monomer is present from about 27 to about 88 percent of the total weight of the monomer content in the polymer.

The invention will be further described by means of the following examples, which are not intended to limit the invention, as defined by the appended claims, in any manner. All weights discussed in the document are expressed in term of dry weight and based on the total weight of the polymer.

EXAMPLES

Preperation of Polymers

Example 1

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 24.0 g of i-Butyl Methacrylate, 12.6 g of Methacrylic Acid, and 39.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 136.0 g of i-Butyl Methacrylate, 71.4 g of Methacrylic Acid, and 221.0 g of t-Octylacrylamide as a 60% solution in Ethanol was added over 3.5 hours using a 1000 mL addition funnel After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 2

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 24.0 g of i-Butyl Methacrylate, 9.6 g of Methacrylic Acid, and 44.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 136.0 g of i-Butyl Methacrylate, 54.4 g of Methacrylic Acid, and 249.3 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to relfux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 3

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 9.6 g of Methacrylic Acid, and 84.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 54.4 g of Methacrylic Acid, and 476.0 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to refux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 4

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 12.6 g of i-Butyl Methacrylate, 11.1 g of Methacrylic Acid, and 61.5 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 71.4 g of i-Butyl Methacrylate, 62.9 g of Methacrylic Acid, and 348.5 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 5

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 12.6 g of Methacrylic Acid, and 79.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 71.4 g of Methacrylic Acid, and 447.7 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 6

To a 2000 mL reaction vessel equipped with an agitator, a heating mantle, a condenser, a 125 mL addition funnel, a 1000 mL addition funnel, and a nitrogen purge was added 60.6 g of i-Propyl Acetate. The stirring was turned on at a rate of 200 rpm, to the reaction was added 2.5 g of Benzoyl Peroxide, 34.4 g of i-Butyl Methacrylate, 14.4 g of Methacrylic Acid, and 52.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 137.6 g of i-Butyl Methacrylate, 57.6 g of Methacrylic Acid, and 208.0 g of t-Octylacrylamide as a 60% solution in Ethanol was added over 3.5 hours using a 1000 mL addition funnel. After this addition was completed, the funnel was rinsed with 4.0 g of Ethanol, which was then added to the reaction. 2 hours and 15 minutes after the start of reflux, 1.1 g of Benzoyl Peroxide dissolved in 84.0 g of i-Propyl Acetate was added over 2 hours. After this addition was completed the funnel was rinsed with 4.0 g of i-Propyl Acetate which was then added to the reaction. The reaction was then allowed to reflux for an additional 8.5 hours. The reaction was then diluted with 108.4 g of i-Propyl Acetate and 25.2 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 7

To a 2000 mL reaction vessel equipped with an agitator, a heating mantle, a condenser, a 125 mL addition funnel, a 1000 mL addition funnel, and a nitrogen purge was added 60.6 g of i-Propyl Acetate. The stirring was turned on at a rate of 200 rpm, to the reaction was added 2.5 g of Benzoyl Peroxide, 26.4 g of i-Butyl Methacrylate, 16.4 g of Methacrylic Acid, and 62.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 105.6 g of i-Butyl Methacrylate, 65.6 g of Methacrylic Acid, and 248.0 g of t-Octylacrylamide as a 60% solution in Ethanol was added over 3.5 hours using a 1000 mL addition funnel. After this addition was completed, the funnel was rinsed with 4.0 g of Ethanol, which was then added to the reaction. 2 hours and 15 minutes after the start of reflux, 1.1 g of Benzoyl Peroxide dissolved in 84.0 g of i-Propyl Acetate was added over 2 hours. After this addition was completed the funnel was rinsed with 4.0 g of i-Propyl Acetate which was then added to the reaction. The reaction was then allowed to reflux for an additional 8.5 hours. The reaction was then diluted with 108.4 g of i-Propyl Acetate and 25.2 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 8

To a 2000 mL reaction vessel equipped with an agitator, a heating mantle, a condenser, a 125 mL addition funnel, a 1000 mL addition funnel, and a nitrogen purge was added 60.6 g of i-Propyl Acetate. The stirring was turned on at a rate of 200 rpm, to the reaction was added 2.5 g of Benzoyl Peroxide, 30.4 g of i-Butyl Methacrylate,15.2 g of Methacrylic Acid, and 57.3 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 121.6 g of i-Butyl Methacrylate, 60.8 g of Methacrylic Acid, and 229.3 g of t-Octylacrylamide as a 60% solution in Ethanol was added over 3.5 hours using a 1000 mL addition funnel. After this addition was completed, the funnel was rinsed with 4.0 g of Ethanol, which was then added to the reaction. 2 hours and 15 minutes after the start of reflux, 1.1 g of Benzoyl Peroxide dissolved in 84.0 g of i-Propyl Acetate was added over 2 hours. After this addition was completed the funnel was rinsed with 4.0 g of i-Propyl Acetate which was then added to the reaction. The reaction was then allowed to reflux for an additional 8.5 hours. The reaction was then diluted with 108.4 g of i-Propyl Acetate and 25.2 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 9

To a 2000 mL reaction vessel equipped with an agitator, a heating mantle, a condenser, a 125 mL addition funnel, a 1000 mL addition funnel, and a nitrogen purge was added 60.6 g of i-Propyl Acetate. The stirring was turned on at a rate of 200 rpm, to the reaction was added 2.5 g of Benzoyl Peroxide, 19.6 g of i-Butyl Methacrylate, 15.2 g of Methacrylic Acid, and 75.3 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 78.4 g of i-Butyl Methacrylate, 60.8 g of Methacrylic Acid, and 301.3 g of t-Octylacrylamide as a 60% solution in Ethanol was added over 3.5 hours using a 1000 mL addition funnel. After this addition was completed, the funnel was rinsed with 4.0 g of Ethanol, which was then added to the reaction. 2 hours and 15 minutes after the start of reflux, 1.1 g of Benzoyl Peroxide dissolved in 84.0 g of i-Propyl Acetate was added over 2 hours. After this addition was completed the funnel was rinsed with 4.0 g of i-Propyl Acetate which was then added to the reaction. The reaction was then allowed to reflux for an additional 8.5 hours. The reaction was then diluted with 108.4 g of i-Propyl Acetate and 25.2 g of Ethanol. The reaction was allowed to reflux an additional 45 minutes, and then cooled to room temperature. The polymer was isolated by making a thin film of the polymer i-Propyl Acetate/ Ethanol solution. The film was allowed to dry at room temperature overnight, then in an oven at 130° C. for 90 minutes. The resulting dry film was then ground up in a blender to isolate the product as a powder.

Example 10

To a 2000 mL reaction vessel equipped with an agitator, a heating mantle, a condenser, a 125 mL addition funnel, a 1000 mL addition funnel, and a nitrogen purge was added 60.6 g of i-Propyl Acetate. The stirring was turned on at a rate of 200 rpm, to the reaction was added 2.5 g of Benzoyl Peroxide, 23.6 g of i-Butyl Methacrylate, 15.2 g of Methacrylic Acid, and 68.7 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 94.4 g of i-Butyl Methacrylate, 60.8 g of Methacrylic Acid, and 274.8 g of t-Octylacrylamide as a 60% solution in Ethanol was added over 3.5 hours using a 1000 mL addition funnel. After this addition was completed, the funnel was rinsed with 4.0 g of Ethanol, which was then added to the reaction. 2 hours and 15 minutes after the start of reflux, 1.1 g of Benzoyl Peroxide dissolved in 84.0 g of i-Propyl Acetate was added over 2 hours. After this addition was completed the funnel was rinsed with 4.0 g of i-Propyl Acetate which was then added to the reaction. The reaction was then allowed to reflux for an additional 8.5 hours. The reaction was then diluted with 108.4 g of i-Propyl Acetate and 25.2 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 11

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 25.8 g of i-Butyl Methacrylate, 14.4 g of Methacrylic Acid, and 19.8 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 146.2 g of i-Butyl Methacrylate, 81.6 g of Methacrylic Acid, and 112.2 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 84.6 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 65.2 g of i-Propyl Acetate and 70.2 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 12

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 7.2 g of Methacrylic Acid, and 88.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 40.8 g of Methacrylic Acid, and 498.7 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 13

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 15.0 g of Methacrylic Acid, and 75.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 85.0 g of Methacrylic Acid, and 425.0 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 14

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 36.0 g of i-Butyl Methacrylate, 9.6 g of Methacrylic Acid, and 42.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 204.0 g of i-Butyl Methacrylate, 54.4 g of Methacrylic Acid, and 238.0 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 15

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 36.0 g of i-Butyl Methacrylate, 12.6 g of Methacrylic Acid, and 19.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 204.0 g of i-Butyl Methacrylate, 71.4 g of Methacrylic Acid, and 107.7 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 16

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 13.8 g of Methacrylic Acid, and 77.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 78.2 g of Methacrylic Acid, and 436.3 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 17

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stiffing was turned on at a rate of 200 rpm, to the reaction was added 2.4 g of Benzoyl Peroxide, 24.0 g of i-Butyl Methacrylate, 12.6 g of Acrylic Acid, and 39.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 136.0 g of i-Butyl Methacrylate, 71.4 g of Acrylic Acid, and 221.0 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 18

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stiffing was turned on at a rate of 200 rpm, to the reaction was added 2.4 g of Benzoyl Peroxide, 24.0 g of i-Butyl Methacrylate, 9.6 g of Acrylic Acid, and 44.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 136.0 g of i-Butyl Methacrylate, 54.4 g of Acrylic Acid, and 249.3 g of t-Octylacrylamide as a 60% solution in Ethanol was added over 3.5 hours using a 1000 mL addition funnel. After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 19

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 9.6 g of Acrylic Acid, and 84.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 54.4 g of Acrylic Acid, and 476.0 g of t-Octylacrylamide as a 60% solution in Ethanol was added over 3.5 hours using a 1000 mL addition funnel After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 20

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 12.6 g of i-Butyl Methacrylate, 11.1 g of Acrylic Acid, and 61.5 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 71.4 g of i-Butyl Methacrylate, 62.9 g of Acrylic Acid, and 348.5 g of t-Octylacrylamide as a 60% solution in Ethanol was added over 3.5 hours using a 1000 mL addition funnel After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Example 21

To a 2000 mL reaction vessel equipped with an agitator, a heating mantle, a condenser, a 125 mL addition funnel, a 1000 mL addition funnel, and a nitrogen purge was added 129.0 g of i-Propyl Acetate. The stirring was turned on at a rate of 200 rpm, to the reaction was added 2.4 g of Benzoyl Peroxide, 12.6 g of Acrylic Acid, and 79.0 g of t-Octylacrylamide as a 60% solution in Ethanol. The reaction was purged with Nitrogen for 15 minutes. The reaction was heated up to reflux, and then the Nitrogen purge was stopped. The reflux was maintained through the course of the reaction. 15 minutes after the start of reflux, a mixture of 71.4 g of Acrylic Acid, and 447.7 g of t-Octylacrylamide as a 60% solution in Ethanol was added over 3.5 hours using a 1000 mL addition funnel After this addition was completed, the funnel was rinsed with 5.0 g of Ethanol, which was then added to the reaction. 2 hours and 15 minutes after the start of reflux, 1.2 g of Benzoyl Peroxide dissolved in 85.4 g of i-Propyl Acetate was added over 2 hours. After this addition was completed the funnel was rinsed with 5.0 g of i-Propyl Acetate which was then added to the reaction. The reaction was then allowed to reflux for an additional 8.5 hours. The reaction was then diluted with 70.9 g of i-Propyl Acetate and 65.9 g of Ethanol. The reaction was allowed to reflux an additional 45 minutes, and then cooled to room temperature. The polymer was isolated by making a thin film of the polymer i-Propyl Acetate/Ethanol solution. The film was allowed to dry at room temperature overnight, then in an oven at 130° C. for 90 minutes. The resulting dry film was then ground up in a blender to isolate the product as a powder.

Compositions of the polymers in Examples 1 to 21 are summarized in Table 1. The weight % is based on the dry weight of the polymer.

TABLE 1

| | Polymer Composition wt. % on a dry basis | | | |
| --- | --- | --- | --- | --- |
| Polymer Example | % i-Butyl Methacrylate | % Methacrylic Acid | % Acrylic Acid | % t-Octyl-acrylamide |
| 1 | 40.0 | 21.0 | 0.0 | 39.0 |
| 2 | 40.0 | 16.0 | 0.0 | 44.0 |
| 3 | 0.0 | 16.0 | 0.0 | 84.0 |
| 4 | 20.8 | 18.3 | 0.0 | 60.9 |
| 5 | 0.0 | 21.0 | 0.0 | 79.0 |
| 6 | 43.0 | 18.0 | 0.0 | 39.0 |
| 7 | 33.0 | 20.5 | 0.0 | 46.5 |
| 8 | 38.0 | 19.0 | 0.0 | 43.0 |
| 9 | 24.5 | 19.0 | 0.0 | 56.5 |
| 10 | 29.5 | 19.0 | 0.0 | 51.5 |
| 11 | 49.5 | 27.6 | 0.0 | 22.8 |
| 12 | 0.0 | 12.0 | 0.0 | 88.0 |

TABLE 1-continued

| Polymer Example | % i-Butyl Methacrylate | % Methacrylic Acid | % Acrylic Acid | % t-Octyl-acrylamide |
|---|---|---|---|---|
| 13 | 0.0 | 25.0 | 0.0 | 75.0 |
| 14 | 50.8 | 13.6 | 0.0 | 35.6 |
| 15 | 60.0 | 21.0 | 0.0 | 19.0 |
| 16 | 0.0 | 23.0 | 0.0 | 77.0 |
| 17 | 40.0 | 0.0 | 21.0 | 39.0 |
| 18 | 40.0 | 0.0 | 16.0 | 44.0 |
| 19 | 0.0 | 0.0 | 16.0 | 84.0 |
| 20 | 20.8 | 0.0 | 18.3 | 60.9 |
| 21 | 0.0 | 0.0 | 21.0 | 79.0 |

Each of the 21 polymer examples and the commercial product Acrylates/Octylacrylamide Copolymer (DERMACRYL® 79, available from Akzo Nobel Surface Chemistry LLC, Bridgewater, N.J.) were made up in the following sunscreen formula.

Sunscreen Formula

To a 250 mL beaker containing a stirred solution of 3.0 g of polymer (see Table 2 below) dissolved in 72.0 g of ethanol was added 3.0 g Avobenzone, 2.0 g Octocrylene, 5.0 g Octisalate, 4.0 g Oxybenzone, 10.0 g Homosalate, and 1.0 g of glycerin. The composition was stirred until all the components were dissolved.

Measurement of In-Vitro SPF

All SPF measurements were conducted using VITRO-SKIN® (IMS Inc. Milford, Conn. and Portland Me., USA) as the substrate to which the sunscreen formulas were applied. Test formulations were applied to the hydrated substrate at 2 mg/cm2 and allowed to dry down for 15 minutes. VITRO-SKIN®, with no formula applied, was used as a reference/blank. The in-vitro SPF of each formula was determined using a Labsphere UV-1000 Ultraviolet Transmittance Analyzer (Labsphere, Inc. North Sutton N.H., USA). A total of 10 in vitro SPF measurements were taken on each formula (two application slides were prepared and 5 measurements were taken on each slide for a total of 10 measurements) using different, non-overlapping positions on the substrate. All SPF values are reported as the average of the 10 measurements for each formula.

Measurement of In-Vivo SPF

Static (without water immersion) SPF and 80 minute water immersion SPF was measured according to FDA, 21 CFR Sec. 201.327, subpart (i), SPF Test Procedure, Sunscreen Drug Products for Over-the-Counter Human Use, Final Monograph, Federal Register, Vol. 76, No. 118, June 17, 2011. Five subjects were tested for each sunscreen formula and an average was determined.

Measurement of Tack

The tack of the dry sunscreen film was measured using a TA XT Plus Texture Analyzer (Texture Technologies, Scarsdale, N.Y.) equipped with a ½ inch diameter acrylic probe. To a ⅝ inch diameter by ⅛ inch deep well in an aluminum plate was added 60 uL of sunscreen. The sunscreen was allowed to dry for 7 1/2 minutes. The probe was lowered onto the film, and then lifted. This was repeated 5 times. The maximum force (in gram force, gmf) to lift the probe was determined. Five runs were done for each sample and the average was calculated.

The in vitro SPF, in vivo static SPF, 80 minute water immersion in vivo SPF, and dry film tack results for the sunscreens made from the 21 polymer examples and DERMACRYL® 79 are shown in Table 2.

TABLE 2

| Sunscreen Example | Polymer | Tack (gmf) | In Vitro SPF | Static In Vivo SPF | 80 Minute Water Immersion In Vivo SPF |
|---|---|---|---|---|---|
| 22 | Example 1 | 249 | 50.9 | | |
| 23 | Example 2 | 296 | 59.7 | | |
| 24 | Example 3 | 314 | 59.6 | | |
| 25 | Example 4 | 371 | 56.4 | | |
| 26 | Example 5 | 398 | 59.9 | | |
| 27 | Example 6 | 305 | 51.2 | | |
| 28 | Example 7 | 260 | 51.7 | | |
| 29 | Example 8 | 300 | 51.5 | | |
| 30 | Example 9 | 333 | 50.4 | | |
| 31 | Example 10 | 224 | 49.1 | | |
| 32 | Example 11 | 317 | 51.9 | | |
| 33 | Example 12 | 458 | 56.0 | | |
| 34 | Example 13 | 251 | 52.6 | | |
| 35 | Example 14 | 366 | 61.2 | 58.4 | 53.0 |
| 36 | Example 15 | 371 | 50.3 | | |
| 37 | Example 16 | 330 | 54.6 | | |
| 38 | Example 17 | 391 | 53.5 | | |
| 39 | Example 18 | 385 | 52.7 | | |
| 40 | Example 19 | 288 | 52.9 | | |
| 41 | Example 20 | 372 | 51.9 | | |
| 42 | Example 21 | 342 | 49.2 | | |
| 43 | Acrylates/Octylacrylamide Copolymer | 466 | 48.6 | 49.6 | 43.3 |

For purposes of the invention, a tack level of 450 gmf or less was considered acceptable tack and above 460 gmf was considered to be unacceptable tack.

Table 2 shows that a sunscreen made using the polymers of this invention provide both higher SPF and lower tack as compared to a sunscreen made using Acrylates/Octylacrylamide Copolymer.

Sunscreen Formula with Varying Levels of UV Absorbers

To a 250 mL beaker containing a stirred solution of 3.0 g of polymer dissolved in ethanol was added 3.0 g Avobenzone, 2.0 g Octocrylene, Octisalate, Oxybenzone, Homosalate, and 1.0 g of glycerin. The composition was stirred until all the components were dissolved. Table 3 shows the polymer used, and amounts of Ethanol, Octisalate, Oxybenzone, Homosalate used.

TABLE 3

| Sunscreen Example | Polymer | Ethanol (grams) | Oxybenzone (grams) | Octisalate (grams) | Homoslate (grams) |
|---|---|---|---|---|---|
| 44 | Example 14 | 79.0 | 2.0 | 3.0 | 7.0 |
| 45 | Example 14 | 78.0 | 2.0 | 4.0 | 7.0 |
| 46 | Example 14 | 79.5 | 2.5 | 3.5 | 5.5 |
| 47 | Example 14 | 80.0 | 3.0 | 4.0 | 4.0 |
| 48 | Example 14 | 81.0 | 3.0 | 3.0 | 4.0 |
| 49 | Example 14 | 82.0 | 2.0 | 3.0 | 4.0 |
| 50 | Example 14 | 78.0 | 3.0 | 3.0 | 7.0 |
| 51 | Example 14 | 81.0 | 2.0 | 4.0 | 4.0 |
| 52 | Example 14 | 77.0 | 3.0 | 4.0 | 7.0 |
| 53 | Acrylates/Octylacrylamide copolymer | 78.0 | 3.0 | 3.0 | 7.0 |

The in vitro SPF, in vivo static SPF and dry film tack results are shown in Table 4.

TABLE 4

| Sunscreen Example | Tack (gmf) | In Vitro SPF | Static In Vivo SPF |
|---|---|---|---|
| 44 | 227 | 40.2 | |
| 45 | 302 | 41.0 | |

TABLE 4-continued

| Sunscreen Example | Tack (gmf) | In Vitro SPF | Static In Vivo SPF |
|---|---|---|---|
| 46 | 266 | 40.7 | |
| 47 | 249 | 43.5 | |
| 48 | 277 | 30.7 | |
| 49 | 261 | 32.1 | |
| 50 | 320 | 54.4 | 47.7 |
| 51 | 228 | 44.6 | |
| 52 | 363 | 43.3 | |
| 53 | 370 | | 36.1 |

Table 4, illustrates the effect of varying the level of sunscreen actives. Sunscreen Example 50 containing polymer Example 14 and sunscreen Example 53 containing Acrylates/Octylacrylamide Copolymer both have the same levels of sunscreen actives. Sunscreen Example 50 still has a higher Static In Vivo SPF and lower tack compared to Sunscreen Example 53.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described herein, the invention is not intended to be limited to the details shown. Rather, various modifications may be made in the details within the range and scope of equivalents of the claims and without departing from the spirit and scope of the invention.

I claim:

1. A skin care formulation comprising:
   (A) a polymer derived from:
   about 12 to about 23 weight percent of the total monomer content of methacrylic acid, and
   a balance of the total monomer content of the N-alkyl (meth)acrylamide monomer: and
   (B) at least one sunscreen active agent,
   wherein said skin care formulation is a non-emulsion, volatile solvent-based formulation.

2. The skin care formulation of claim 1 wherein the N-alkyl (meth)acrylamide monomer is selected from the group consisting of N-n-octylacrylamide, N-t-octylacrylamide and mixtures thereof.

3. The skin care formulation of claim 1 wherein the polymer is present in an amount of 0.1 to 8% by weight of the formulation.

4. The skin care formulation of claim 1 wherein the sunscreen active agent is present in an amount of 50% or less by weight of the formulation.

5. The skin care formulation of claim 1 wherein the formulation has a tack level of 450 gmf (gram force) or less.

6. A method of reducing the deleterious effects of UV radiation that contacts a surface comprising:
   applying to the surface the skin care formulation of claim 1.

* * * * *